(12) United States Patent
Yu et al.

(10) Patent No.: US 10,702,867 B2
(45) Date of Patent: Jul. 7, 2020

(54) MICROFLUIDICS SENSING SYSTEM

(71) Applicant: Hewlett-Packard Development Company, L.P., Houston, TX (US)

(72) Inventors: Joshua M. Yu, Corvallis, OR (US); Matthew David Smith, Corvallis, OR (US); Shameed Sait M A, Bangalore (IN); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 109 days.

(21) Appl. No.: 15/521,230

(22) PCT Filed: Jun. 29, 2015

(86) PCT No.: PCT/US2015/038282
§ 371 (c)(1),
(2) Date: Apr. 21, 2017

(87) PCT Pub. No.: WO2016/122705
PCT Pub. Date: Aug. 4, 2016

(65) Prior Publication Data
US 2017/0341076 A1 Nov. 30, 2017

(30) Foreign Application Priority Data
Jan. 30, 2015 (IN) .............................. 475/CHE/2015

(51) Int. Cl.
*B01L 3/00* (2006.01)
*G01N 35/00* (2006.01)
(Continued)

(52) U.S. Cl.
CPC .. *B01L 3/502715* (2013.01); *G01N 33/48792* (2013.01); *G01N 35/00871* (2013.01);
(Continued)

(58) Field of Classification Search
CPC ....... B01L 3/502715; B01L 2400/0487; B01L 2200/148; B01L 2200/147; B01L 2200/14;
(Continued)

(56) References Cited

U.S. PATENT DOCUMENTS

2002/0015667 A1    2/2002   Chow
2009/0209911 A1    8/2009   Cabus et al.
(Continued)

FOREIGN PATENT DOCUMENTS

CN      1226845      8/1999
CN    101416048      4/2009
(Continued)

OTHER PUBLICATIONS

Peter B. Lillehoj et al: "Rapid electrochemical detection on a mobile phone", Lab on a Chip, vol. 13, No. 15, May 10, 2013 (May 10, 2013), pp. 2950-2955, XP055480817.
(Continued)

*Primary Examiner* — Samuel P Siefke
(74) *Attorney, Agent, or Firm* — Perry + Currier Inc (57) ABSTRACT

Example implementations relate to a microfluidics sensing system. For example, a microfluidics sensing system may include a portable computing device to execute a microfluidics application, a microfluidic chip coupled to the portable computing device, the microfluidic chip including a microfluidic pumping and sensing region to perform a test on a biologic sample, and a printed circuit board (PCB) on a microfluidic reader to instruct the microfluidic pumping and sensing region to perform the test based on a command received from the microfluidics application.

7 Claims, 5 Drawing Sheets

(51) Int. Cl.
*G01N 33/487* (2006.01)
*G16H 10/40* (2018.01)

(52) U.S. Cl.
CPC .......... *G16H 10/40* (2018.01); *B01L 2200/14* (2013.01); *B01L 2200/147* (2013.01); *B01L 2200/148* (2013.01); *B01L 2400/0487* (2013.01)

(58) Field of Classification Search
CPC ....... G01N 33/48792; G01N 35/00871; G16H 40/40
See application file for complete search history.

(56) References Cited

U.S. PATENT DOCUMENTS

| | | |
|---|---|---|
| 2012/0271655 A1 | 10/2012 | Knobel et al. |
| 2013/0273524 A1 | 10/2013 | Ehrenkranz |
| 2013/0346026 A1 | 12/2013 | Teich |
| 2014/0273187 A1 | 9/2014 | Johnson et al. |

FOREIGN PATENT DOCUMENTS

| | | |
|---|---|---|
| WO | WO-2014040185 | 3/2014 |
| WO | WO-2014047137 A1 | 3/2014 |
| WO | WO-2014123998 A2 | 8/2014 |
| WO | WO-2014127091 A1 | 8/2014 |
| WO | WO-2014144548 | 9/2014 |
| WO | WO-2014178827 | 11/2014 |
| WO | WO-2015116083 A1 | 8/2015 |
| WO | WO-2015116956 A1 | 8/2015 |

OTHER PUBLICATIONS

Xinhao Wang et al: "Audio jack based miniaturized mobile phone electrochemical sensing platform", Sensors and Actuators B: Chemical: International Journal devoted to Research and Development of physical and chemical Transducers vol. 209.

Duval, et al.; Silicon Photonic Based Biosensors: the Future of Lab-on-a-chip Diagnostic Devices; www.PhotonicsSociety.org.; Aug. 2012, vol. 26, No. 4.; pp. 1-40.

MICROFLUIDICS SENSING SYSTEM

BACKGROUND

Microfluidics is a technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and DNA, detecting biochemical toxins and pathogens, diagnosing diseases, etc.

DETAILED DESCRIPTION

Microfluidic chips may be employed in point of care testing to enable assay operations at a location associated with an individual to be tested. For example, in various point of care approaches to microfluidic testing a sample may be analyzed by a sensor in microfluidic testing device to give an indication of a disease state, among other possible conditions.

A living cell is the basic structural and functional unit of an organism. Most animal and plant cells range in size from 1-100 micrometers and contain vital health information. Cell-based diagnostics may be used for detecting infectious diseases (HIV, Malaria, Tuberculosis), as well as chronic diseases (cancer, cardiac diseases, autoimmune diseases). Traditional cellular level diagnostic tools may, for example, be expensive, involve specialized training to operate, and may not always be deployed at the point-of-care setting. Furthermore, healthcare is gradually migrating away from centralized hospitals to a more distributed and/or in-home settings. This transition may, for example, involve the use of technology that provides the same level of performance and functionality as tests that are done in hospitals using sophisticated machinery, although in a smaller and more portable form.

A microfluidics sensing system in accordance with the present disclosure may, for example, provide laboratory level diagnostic performance at the convenience of a household and/or a remote setting. As described further herein, a test may be initiated, powered and driven by a microfluidics application on a portable computing device. The microfluidics application may direct a microfluidic chip that has embedded pumps, drop ejectors, impedance sensors and/or thermal sensors among other components to perform a test on a biologic sample. The microfluidics sensing system in accordance with the present disclosure may allow digital data to be captured and analyzed on a portable computing device, and may allow results to be provided to healthcare providers, patients, and/or other users in a shorter period of time and at a lower cost as compared to hospital diagnostic tests.

For purposes of this disclosure, the term "microfluidic" refers to devices and/or passages which interact with fluids having a volume or carrying particles having dimensions in the "micro" range, microliter or micrometer, respectively. For purposes of this disclosure, the term "particle" encompasses any small minute piece, fragment or amount, including, not limited to, a biological cell or group of biological cells. A "fluid" may comprise a liquid, a gas or mixtures thereof. Additionally, a "biologic sample" refers to a solution including blood and/or blood components such as blood plasma and/or blood serum, as well as a solution containing biomarker not derived from blood, such as bacteria, yeast, fungi and viruses, among other components.

Figure 1:
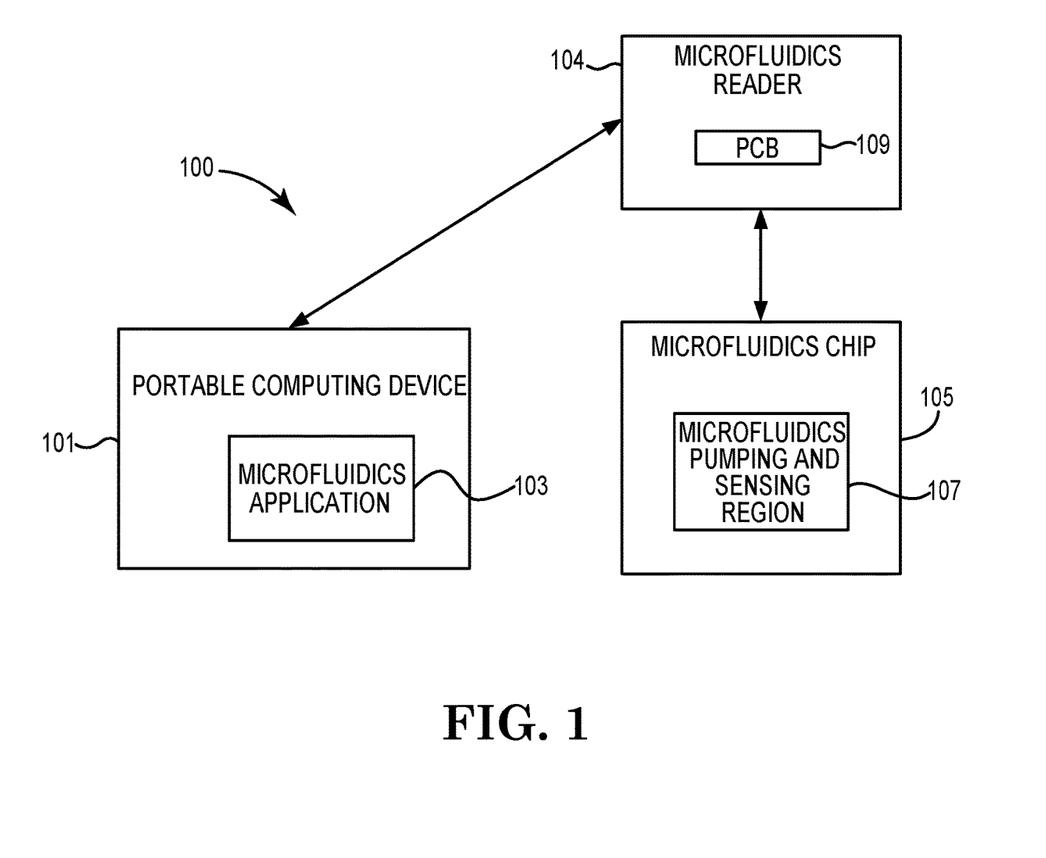
FIG. 1 illustrates an example of a microfluidics sensing system, according to the present disclosure.

FIG. 1 illustrates an example of a microfluidics sensing system 100, according to the present disclosure. As illustrated in FIG. 1, the microfluidics sensing system 100 may include a portable computing device 101 to execute a microfluidics application 103. As used herein, a microfluidics application may refer to a program having instructions to perform particular tasks. Additionally, the microfluidics sensing system 100 may include a microfluidic chip 105 coupled to the portable computing device 101. The microfluidic chip 105 including a microfluidic pumping and sensing region 107 to perform a test on a biologic sample, such as a fluid sample received on the microfluidic chip 105. As used herein, a microfluidic pumping and sensing region refers to a specialized portion of the microfluidic chip 105 configured to channel the flow of the fluid sample over a series of sensors, using specialized pumps. Additionally, the microfluidic chip 105 may be coupled to a microfluidic reader 104 which may include a printed circuit board (PCB) 109 that is to instruct the microfluidic pumping and sensing region 107 to perform the test based on a command received from the microfluidics application 103. For example, the microfluidics application 103 may provide instructions to the microfluidic reader 104, which may subsequently provide instructions to the microfluidics chip 105 to perform a thermal sensing test. While FIG. 1 illustrates the microfluidic reader 104 and the microfluidic chip 105 as separate and independent components, examples are not so limited. In some examples, the microfluidic chip 105 could be on the PCB 109, and the PCB 109 could directly connect to the portable computing device 101 (e.g., via a universal serial bus (USB) cable). Additionally and/or alternatively, the microfluidic reader 104 may be a part of the portable computing device 101, and the portable computing device 101 may be configured to receive the microfluidic chip 105 (and/or the cassette, as discussed in relation to FIG. 2).

The microfluidics sensing system 100 may also include an application programming interface (API) in communication with the PCB 109 which may receive instructions from the microfluidics application to perform the test on the biologic sample. For instance, a user may initiate the microfluidics application 103 on the portable computing device 101. In response to initiation of the microfluidics application 103, the API may be invoked. For instance, the microfluidics application 103, which may reside on the portable computing device 101, may execute an operating system (OS) as discussed further in relation to FIG. 2. The microfluidics application 103 may be an Android application, a Windows application, and an iOS application, among other types of applications. The microfluidics application 103 may be selected, opened, activated, and/or initiated by a user of the microfluidics application 103, which may then invoke the API for a specific test of interest. The API may then communicate with hardware with instructions on the PCB 109, which may then send signals to the microfluidic chip to perform various tests. In such a manner, the microfluidics application may provide instructions to hardware with instructions on the microfluidic reader to perform the test. The microfluidic chip 105 may also be plug compatible with standard interfaces. For instance, the microfluidic reader 104 and portable computing device 101 may include any standard interface which may be coupled to the microfluidic chip 105.

In some examples, the microfluidic chip 105 may be powered by the portable computing device 101. For example, as discussed in relation to FIG. 2, the microfluidic chip 105 may include an electrical interface which may receive power from the portable computing device 101. In some examples, the microfluidics chip 105 may receive power from the portable computing device 101 via a microfluidic reader, USB device, and/or other device capable of transmitting power and/or information. The power received from the portable computing device 101 may power a test being performed on the microfluidic chip 105, which may be performed at a voltage less than 15V. However examples are not so limited, and tests may be performed on the microfluidic chip 105 at voltages greater and less than 15V.

Figure 2:
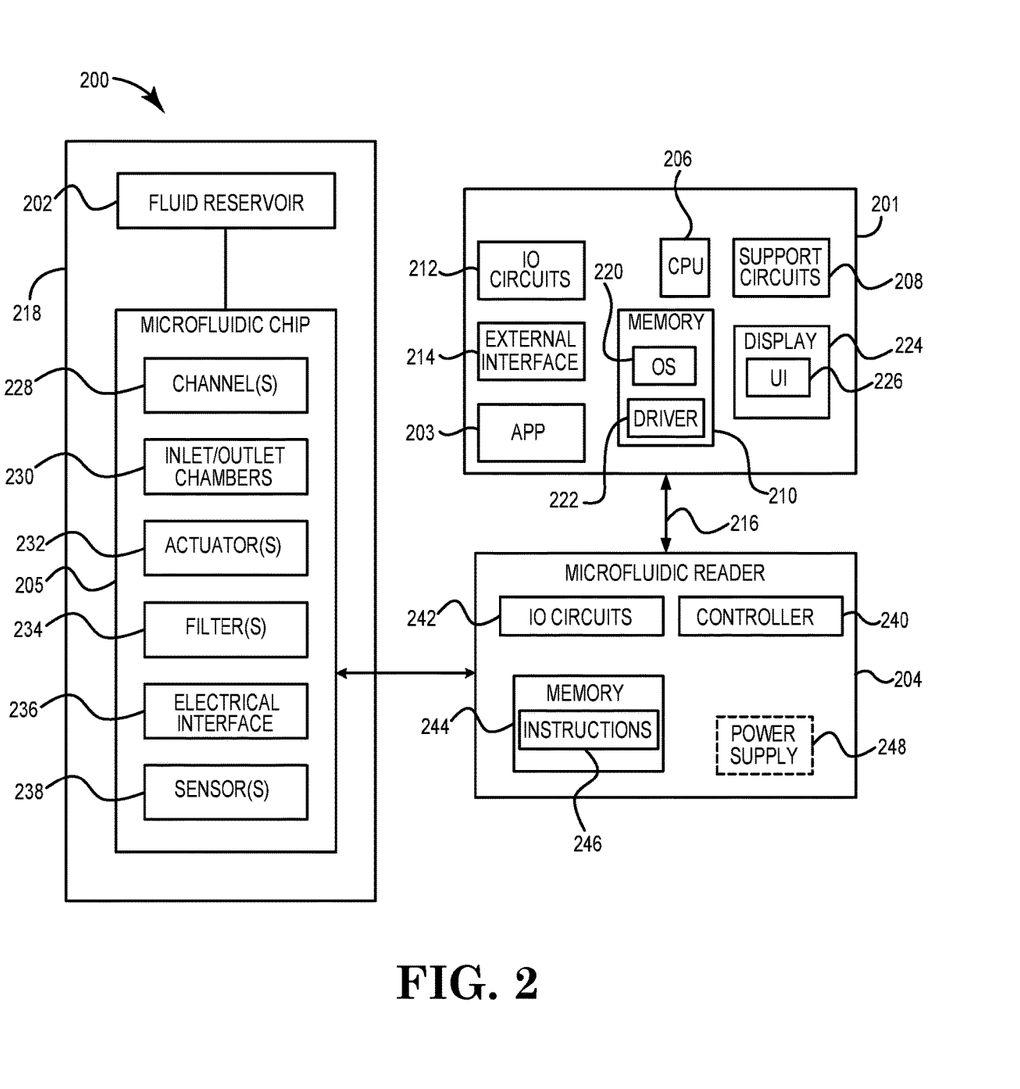
FIG. 2 illustrates an example of a microfluidics sensing system, according to the present disclosure.

FIG. 2 illustrates an example of a microfluidics sensing system 200, according to the present disclosure. As illustrated in FIG. 2, the microfluidic sensing system 200 includes a microfluidic chip 205, a fluid reservoir 202, a microfluidic reader 204, and a portable computing device 201. In general, a sample of fluid may be placed in the fluid reservoir 202. The fluid may be a host fluid having particles (e.g., a blood sample, an ink containing pigments/particles, or the like). As discussed further herein, the fluid may be processed through microfluidics on the microfluidic chip 205 and applied to a sensor in the microfluidic chip 205 under control of the microfluidic reader 204 and the portable computing device 201. The microfluidic chip 205 may provide an electrical output signal representing sensed data to the microfluidic reader 204.

As discussed further herein, the microfluidic reader 204 may be under control of the portable computing device 201. The portable computing device 201 may send and receive data to and from the microfluidic reader 204, including command information for controlling the microfluidic chip 205 and sensor data obtained from the microfluidic chip 205.

The portable computing device 201 generally includes a central processing unit (CPU) 206, various support circuits 208, memory 210, various input/output (I/O) circuits 212, and an external interface 214. A microfluidics application 203 may be installed on the portable computing device 201, as discussed in relation to FIG. 1. As used herein, a microfluidics application refers to instructions executed by a processing resource that direct the processing resource to perform a microfluidics sensing test. For example, the microfluidics application 203 includes instructions executed by the microfluidic reader 204 and microfluidic chip 205 to perform a microfluidics sensing test. The support circuits 208 may include cache, power supplies, clock circuits, data registers, and the like. The memory 210 may include random access memory, read only memory, cache memory, magnetic read/write memory, and/or any combination of such memory devices. The I/O circuits 212 may cooperate with the external interface 214 to facilitate communication with the microfluidic reader 204 over a communication medium 216. The communication medium 216 may be any type of transfer path, including an electrical, optical, and/or radio frequency (RF) path, among others.

The external interface 214 may include a universal serial bus (USB) controller capable of sending and receiving data to the microfluidic reader 204, as well as providing power to the microfluidic reader 204, over a USB cable. However, examples are not so limited, and the microfluidic reader 204 may receive power from an internal power supply 248, as discussed further herein. In some examples, the microfluidic reader 204 may be referred to as a dongle, and may include a number of components enabling the portable computing device 201 to send, collect, and receive data using the microfluidic chip 205. Further, the microfluidic reader 204 may be configured to receive a cassette 218 coupled to the microfluidic chip 205. For example, the microfluidic chip 205 may be mechanically inserted into the cassette 218, and the cassette 218 (having the microfluidic chip 205 coupled) may be inserted into the microfluidic reader 204.

The memory 210 may store an operating system (OS) 220 and a driver 222. The OS 220 and the driver 222 may include instructions executable by the CPU 206 for controlling the portable computing device 201 and the microfluidic reader 204 through the external interface 214. The driver 222 may provide an interface between the OS 220 and the microfluidic reader 204. Accordingly, the portable computing device 201 may comprise a programmable device that includes machine-readable instructions stored in the form of software modules, for example, on non-transitory processor/computer readable-media (e.g., the memory).

The portable computing device 201 may further include a display 224 through which the OS 220 may provide a user interface (UI) 226. A user may use the UI 226 to interact with the OS 220 and the driver 222 to control the portable computing device 201, microfluidic reader 204, and/or the microfluidic chip 205. For example, the user may use the UI 226 to initiate the microfluidics application 203, and select a test to perform on a biologic sample, using the microfluidic chip 205. As used herein, a user may refer to a healthcare professional and/or a patient. However, examples are not so limited, and a user may refer to any type of user other than healthcare professionals and patients.

The portable computing device 201 may also display data received from the microfluidic reader 204. For instance, the portable computing device 201 may display a graphical user interface associated with the microfluidics application 203, as well as data collected, displayed, and/or analyzed by the microfluidic chip 205 and/or microfluidic reader 204. In some examples, data displayed on the UI 226 of the portable computing device 201 may include a diagnosis, such as diagnosis of a particular disease state such as diabetes, human immunodeficiency virus (HIV), and bladder cancer, among others. Additionally and/or alternatively, data displayed on the UI 226 of the portable computing device 201 may include a graph, table, and/or other summary describing data collected using the microfluidic chip 102. For example, the UI 226 of the portable computing device 201 may display data indicating a rate of coagulation of a blood sample, the presence and/or absence of particular antibodies in a particular blood sample, and/or blood glucose levels, among others. Examples are not so limited, however, and the UI 226 of the portable computing device 201 may display other forms of data collected with the microfluidic chip 205 and/or microfluidic reader 204. In some examples, the portable computing device 201 may be a device such as a "smart phone", a tablet computer, or other device.

The fluid reservoir 202 may be in fluidic communication with the microfluidic chip 205. In some examples, the fluid reservoir 202 is an external fluid reservoir, meaning that the fluid reservoir 202 is external to the microfluidic chip 205. For instance, the fluid reservoir 202 may be on the cassette 218 configured to receive the microfluidic chip 205. However, examples are not so limited, and the fluid reservoir 202 and/or a portion of the fluid reservoir 202 may be located on the microfluidic chip 205 itself (e.g., not on the cassette 218). For instance, a lower portion of the fluid reservoir 202 may be located on the microfluidic chip 205, while an upper portion of the fluid reservoir 202 may be located on the cassette 218.

In some examples, the fluid reservoir 202 may be configured to hold and supply fluidic components/samples and/or solutions to the microfluidic chip 205. Various examples of the microfluidic chip 205 are described further herein and may generally include inlet/outlet chamber(s) 230, microfluidic channel(s) 228, actuator(s) 232, microfluidic filter(s) 234, sensor(s) 238, and an electrical interface 236. As described in relation to FIG. 1, the microfluidic reader 204 may be coupled to the electrical interface 236 and may provide power (via the portable computing device 201) to the actuator(s) 232 and/or sensor(s) 238. In general, the structures and components of the microfluidic chip 205 may be fabricated using conventional integrated circuit microfabrication techniques such as thin film deposition, electroforming, laser ablation, anisotropic etching, sputtering, dry and wet etching, photolithography, casting, molding, stamping, machining, spin coating, laminating, and so on. Furthermore, the microfluidic chip 205 may be composed of a number of materials. For instance, the microfluidic chip 205 may include a bulk silicon substrate which is microfabricated to form the microfluidic channels 228 and/or the sensor(s) 238. Additionally, the microfluidic chip 205 may include microfluidic channels 228 formed out of a photo imagable polymer, such as SU-8.

As described in relation to FIG. 1, the microfluidic chip 205 may include a microfluidic pumping and sensing region. As used herein, the microfluidic pumping and sensing region (e.g., 107 illustrated in FIG. 1) may include the microfluidic channels 228, inlet/outlet chambers 230, actuators 232, filters 234, electrical interface 236, and/or sensors 238.

The microfluidic reader 204 may be coupled to the microfluidic chip 205 and may enable transmission of information and power between the portable computing device 201 and the microfluidic chip 205. In some examples, the microfluidic reader 204 may include a controller 240, I/O circuits 242, and a memory 244. Further, the microfluidic reader 204 may receive power from the portable computing device 201, such as through a USB cable. However, examples are not so limited, and the microfluidic reader 204 may include a power supply 248.

The memory 244 may store hardware with instructions 246, which may include instructions executable by the controller 240 for controlling the microfluidic chip 205 and communicating with the portable computing device 201. For example, the hardware with instructions 246 may include instructions executable by the controller 240 for controlling the sensors 238 on the microfluidic chip 205. Accordingly, the microfluidic reader 204 may comprise a programmable device that includes machine-readable instructions, for example, on non-transitory processor/computer readable-media (e.g., the memory). All or a portion of the microfluidic reader 204 may be implemented using a programmable logic device (PLD), application specific integrated circuit (ASIC), or the like.

In some examples, the microfluidic chip 205 may include a plurality of sensors 238. For instance, the microfluidic chip 205 may include a single sensor 238, or more than one sensor 238. Furthermore, the microfluidic chip 205 may include a plurality of types of sensors 238. For example, the sensor(s) 238 may be thermal sensors which may detect and/or report a temperature of the microfluidic chip 205 to the microfluidic reader 204. In another example, the sensor(s) 238 may be electrochemical sensors which may measure an amount of a chemical compound in a fluid sample at a particular point in time. In yet another example, the sensor(s) 238 may be antibody detecting sensors which may measure an amount of an antigen in a fluid sample at a particular point in time. Further, the sensor(s) 238 may be coagulation sensors which may measure an amount of blood clotting components in a fluid sample at a particular point in time.

In an example, the sensor(s) 238 may be disposed in the channel(s) 228 near inlet(s) of the channel(s) 228 (e.g., closer to the fluid reservoir 202 than the actuator(s) 232). In another example, the sensor(s) 238 may be disposed in the inlet of the channel(s) 228. The sensor(s) 238 may be an impedance sensor formed using various semiconductor formation techniques. The sensor(s) 238 may detect impedance changes as particles in the fluid sample pass over and/or near the sensor(s) 238. Examples are not so limited, however, and the sensor(s) 238 may be optical sensors that convert light rays into an electrical signal and/or other types of sensors that are capable of performing a particular test on the fluid sample.

Further, the actuator(s) 232 may be disposed near a closed end of the channel(s) 228 downstream from the sensors 238. The actuator(s) 232 may be implemented using a wide variety of structures suitable to communicate a fluid sample through the channels 228. For example, the actuator(s) 232 may be a thermal resistor(s) that produces vapor bubbles to create fluid displacement of the fluid sample within the channel(s) 228. Actuators 232 may also be implemented as piezo elements (e.g., PZT) whose electrically induced deflections generate fluid displacements within the channel(s) 228. Other deflective membrane elements activated by electrical, magnetic, and other forces are also possible for use in implementing the actuator(s) 232. The displaced fluid sample may be ejected from nozzle(s) on the microfluidic chip 205. A nozzle may refer to an ejection nozzle suitable for use with actuator(s) 232. Further, the nozzle(s) may be disposed in or along the channel(s) 228. For example, nozzle(s) 228 may be adjacent to the sensor(s) 238 in the channel(s) 228.

In some instances, the microfluidic chip 205 may be a specialized microfluidic chip, wherein the microfluidic chip 205 includes microfluidic channels 228 and sensors 238 to perform a particular test. For example, the microfluidic chip 205 may be specialized for performing antigen detection, and may include a surface coated with a particular antibody which is capable of binding to a specified antigen. In such an example, the sensors 238 may be specialized sensors designed to detect the presence of the particular antigen-antibody conjugate. In another example, the microfluidic chip 205 may be specialized for performing a coagulation test, and may include sensors 238 designed to detect the presence of various components present in a blood clotting cascade.

In some examples, the microfluidic reader 204 may detect a type of microfluidic chip 205 coupled to the microfluidic reader 204 (e.g., via the cassette 218), and may instruct the microfluidic application 203 accordingly. For instance, the microfluidic reader 204 may send information to the microfluidic application 203, via the portable computing device 201, indicating that a blood glucose chip has been coupled to the microfluidic reader 204, and that the microfluidic application 203 should be configured for blood glucose tests. In another example, the microfluidic reader 204 may send information to the microfluidic application 203, via the portable computing device 201, indicating that a coagulation chip has been coupled to the microfluidic reader 204, and that the microfluidic application 203 should be configured for coagulation tests. Examples are not so limited, however, and the microfluidic application 203 may receive input from a user, directing a type of test to be performed by the microfluidic chip 205. For instance, the microfluidics application 203 may provide instructions to the microfluidic reader 204 and/or the microfluidic chip 205, identifying a particular test that is to be performed. For instance, a user of the portable computing device 201 may, using the microfluidics application 203, select a particular test to be performed (e.g., coagulation sensing). In response to the user selecting the particular test to be performed on the microfluidic chip 205, the portable computing device 201 and the microfluidic reader 204 may direct the microfluidic chip 205 to perform the particular test (e.g., coagulation sensing).

In some examples, the microfluidic chip 205 may include a plurality of microfluidic channels 228 and a plurality of types of sensors 238. For instance, the microfluidic chip 205 may include sensors 238 to perform thermal sensing tests, as well as sensors 238 to perform coagulation tests.

While the above described elements and configurations are illustrated in FIG. 2 the present disclosure is not so limited. Rather, more or less components may be included in the microfluidic sensing system 200, in the microfluidic chip 205, a microfluidic reader 204, and a portable computing device 201 and/or arranged in various configurations, as described herein. Additionally while a particular number of elements are illustrated (e.g., a single channel 228) there may be more (e.g., two or more channels 228) and/or less of various elements such as the fluid reservoir 202, the channel(s) 228, the actuator(s) 232, filters(s) 234, the electrical interface 236, the sensor(s) 238, etc. depending upon a desired application of the microfluidic sensing system 200.

Figure 3:
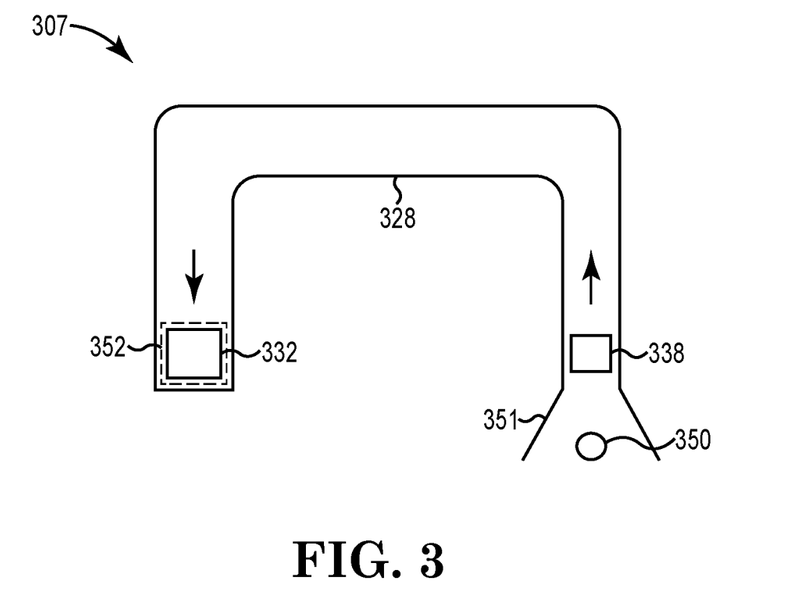
FIG. 3 illustrates a schematic diagram of an example of a portion of a microfluidic pumping and sensing region, according to the present disclosure.

FIG. 3 illustrates a schematic diagram of an example of a portion of a microfluidic pumping and sensing region 307, according to the present disclosure. The portion of the microfluidic pumping and sensing region 307 includes a channel 328 (i.e., a microfluidic channel), an actuator 332, a sensor 338, an inlet 351 to receive a fluid sample 350, and a nozzle 352 (e.g., an outlet from the channel 328). In an example, a filter (e.g., a mesh filter) may be provided for filtering particles in the applied fluid sample. While the shape of the fluid channel 328 is shown as being "u-shaped", this is not intended as a limitation on the shape of the channel 328. Thus, the shape of the channel 328 may include other shapes, such as curved shapes, snake-like shapes, shapes with corners, combinations thereof, and so on. Moreover, the channel 328 is not shown to any particular scale or proportion. The width of the channel 328 as fabricated on a device may vary from any scale or proportion shown in the drawings of this disclosure. The arrows in the channel indicate an example of a direction of fluid flow of a fluid sample through the channel 328.

The inlet 351 may provide an opening for the channel 328 to receive the fluid sample. In some examples, the inlet 351 may have a larger width and volume than the channel 328. That is, a volume of the inlet 351 may be greater than a volume of the channel 328.

In some examples, the sensor 338 is disposed in the channel 328. The sensor 338 may be an impedance sensor formed using various semiconductor techniques. The sensor 338 may detect impedance changes as particles in the fluid sample pass over the sensor 338.

The actuator 332 may be disposed near a closed end of the channel 328 downstream from the sensor 338. The actuator 332 may be a fluidic inertial actuator, which may be implemented using a wide variety of structures. For example, the actuator 332 may be a thermal resistor that produces vapor bubbles to create fluid displacement within the channel 328. The displaced fluid sample may be ejected from the nozzle(s) 352.

Figure 4:
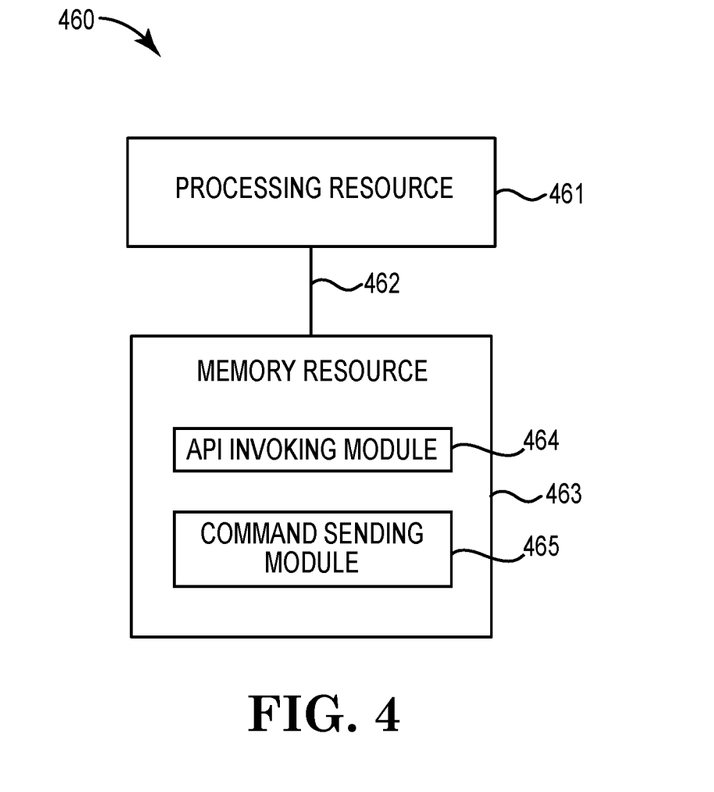
FIG. 4 illustrates an example of a computing device for operating a microfluidics sensing system, according to the present disclosure.

FIG. 4 illustrates an example of a computing device 460 for operating a microfluidics sensing system according to the present disclosure. The microfluidics sensing system may include a processing resource 461 connected via a connection 462 to a memory resource 463, e.g., a computer-readable medium (CRM), machine readable medium (MRM), database, etc. In some examples, memory resource 463 may be a non-transitory storage medium and/or a non-transitory machine readable medium, where the term "non-transitory" does not encompass transitory propagating signals.

The memory resource 463 may include a plurality of computing modules. As used herein, a computing module may include computer executable instructions, hardware components (e.g., various forms of transistor logic, application specific integrated circuits (ASICs), etc.), or a combination thereof. But a computing module at least includes instructions executable by the processing resource (e.g., in the form of modules) to perform particular actions, tasks, and tests described in more detail herein in reference to FIGS. 1-3.

In some examples, the memory resource 463 may include an API invoking module 464. The API invoking module 464 may include instructions that when executed by the processing resource 461 may invoke an API in communication with a PCB on a microfluidic reader. For instance, the memory resource 463 may include instructions that when executed by the processing resource 461 may invoke an API in communication with a PCB on microfluidic reader 104 illustrated in FIG. 1, and 204 illustrated in FIG. 2. In response to receiving commands from the API, the PCB on the microfluidic reader may send signals to the microfluidic chip to perform various tests thereon. As described in relation to FIGS. 1 and 2, the microfluidic chip may include a surface to receive a biologic sample and a microfluidic pumping and sensing region (e.g., microfluidic pumping and sensing region 107 illustrated in FIG. 1) to perform a test on the biologic sample.

Further, the memory resource 463 may include a command sending module 465. The command sending module 465 may include instructions that when executed by the processing resource 461 may send a command from the API to the PCB on the microfluidic reader (e.g., microfluidic reader 104 in FIG. 1, and 204 in FIG. 2), and from the microfluidic reader to the microfluidic chip, instructing the microfluidic pumping and sensing region on the microfluidic chip to perform the test on the biologic sample.

In one example, the command sending module 465 may include may include instructions that when executed by the processing resource 461 may send a command from the API to the PCB on the microfluidic reader, and from the microfluidic reader to the microfluidic chip, instructing the microfluidic chip to perform a coagulation test on the biologic sample. However, examples are not so limited, and the command sending module 465 may include may instruct the microfluidic chip to perform a number of other tests. For example, the command sending module 465 may include instructions that when executed by the processing resource 461 may send a command from the API to the PCB on the microfluidic reader, and from the microfluidic reader to the microfluidic chip, directing the microfluidic pumping and sensing region on the microfluidic chip to perform a fluidic pumping test. As used herein, a fluidic pumping test refers to performing particular tests for operating the microfluidic channels, nozzles, and/or actuators within the microfluidic chip.

In another example, the command sending module 465 may include instructions that when executed by the processing resource 461 may send a command from the API to the PCB on the microfluidic reader, and from the microfluidic reader to the microfluidic chip, directing the microfluidic pumping and sensing region on the microfluidic chip to perform a fluid ejection test. As used herein, a fluid ejection test refers to ejecting a biologic sample from the nozzles in the microfluidic chip.

In yet another example, the command sending module 465 may include instructions that when executed by the processing resource 461 may send a command from the API to the PCB on the microfluidic reader, and from the microfluidic reader to the microfluidic chip, directing the microfluidic pumping and sensing region on the microfluidic chip to perform an impedance sensing test. As used herein, an impedance sensing test refers to sensing a change in impedance using the sensors in the microfluidic chip, in response to passage of a sample over the sensors, as described in relation to FIG. 3.

Similarly, the command sending module 465 may include instructions that when executed by the processing resource 461 may send a command from the API to the PCB on the microfluidic reader, and from the microfluidic reader to the microfluidic chip, directing the microfluidic pumping and sensing region on the microfluidic chip to perform a thermal control test. As used herein, a thermal control test refers to detecting and/or regulating the temperature of the microfluidic chip.

Additionally, the command sending module 465 may include instructions that when executed by the processing resource 461 may send a command from the API to the PCB directing microfluidic pumping and sensing region to perform at least one of a mixing test and an incubation test. As used herein, a mixing test refers to mixing a biological sample with a particular component and/or mixture, such as an antibody tag, for performing a particular assay. Also, as used herein, an incubation test refers to allowing the biological sample, with or without mixing, to incubate in the channels of the microfluidic chip for a defined period of time.

Although examples are given herein defining distinct tests to be performed on the microfluidic chip, examples are not so limited. For instance, the command sending module 465 may include instructions that when executed by the processing resource 461 may send a command from the API to the PCB on the microfluidic reader, and from the microfluidic reader to the microfluidic chip, instructing the microfluidic chip to perform a combination of tests, such as fluidic pumping, fluid ejection, impedance sensing, among other combinations.

Figure 5:
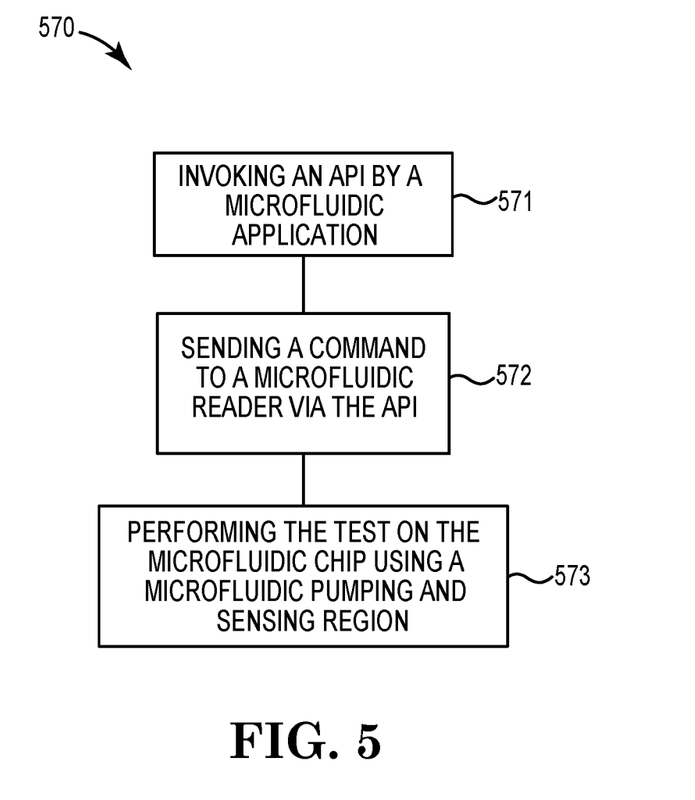
FIG. 5 illustrates an example of a method of microfluidic sensing, according to the present disclosure.

FIG. 5 illustrates an example of a method 570 of microfluidic sensing according to the present disclosure. At 571, the method 570 may include invoking an API by a microfluidic application. For example, as discussed in relation to FIG. 2, the microfluidic application 203 may invoke the API.

At 572 the method 570 may include sending a command to a microfluidic reader via the API, the command specifying a test to be performed on the microfluidic chip. For instance, the API may communicate with the hardware with instructions on the microfluidic reader (e.g., microfluidic reader 204 illustrated in FIG. 2), which may control the microfluidic chip. The API may send the command to the microfluidic reader specifying a particular test to be performed (e.g., coagulation test) and/or a combination of tests to be performed (e.g., mixing and incubation tests).

At 573 the method 570 may include performing the test on the microfluidic chip using a microfluidic pumping and sensing region on the microfluidic chip. For example, as discussed in relation to FIGS. 1, 2, and 3, the microfluidic pumping and sensing region of the microfluidic chip refers to the portion of the microfluidic chip including the microfluidic channels, inlet/outlet chambers, actuators, filters, sensors, and nozzles. In response to receiving instructions from the microfluidic application (e.g., microfluidic application 203 illustrated in FIG. 2), the microfluidic pumping and sensing region may perform the specified tests. In some examples, as discussed further herein, the test and/or tests may be performed at a low voltage, for instance, at a voltage between 5V and 15V.

In the present disclosure, reference is made to the accompanying drawings that form a part hereof, and in which is shown by way of illustration how a number of examples of the disclosure may be capable of being practiced. These examples are described in sufficient detail to enable those of ordinary skill in the art to practice the examples of this disclosure, and it is to be understood that other examples may be capable of being used and that process, electrical, and/or structural changes may be capable of being made without departing from the scope of the present disclosure.

The figures herein follow a numbering convention in which the first digit corresponds to the drawing figure number and the remaining digits identify an element or component in the drawing. Elements shown in the various figures herein may be capable of being added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense.

Further, as used herein, "a" or "a number of" something may refer to one or more such things. For example, "a number of widgets" may refer to one or more widgets. Also, as used herein, "a plurality of" something may refer to more than one of such things.

The above specification, examples and data provide a description of the method and applications, and use of the system and method of the present disclosure. Since many examples may be capable of being made without departing from the spirit and scope of the system and method of the present disclosure, this specification merely sets forth some of the many possible example configurations and implementations.

What is claimed is:
1. A microfluidics sensing system, comprising:
 a portable computing device including a processor programmed to execute a microfluidics application, the processor to execute the microfluidics application to invoke an application programming interface (API) to perform a test on a biologic sample;

a microfluidic chip to be coupled to the portable computing device, the microfluidic chip including a microfluidic pumping and sensing region to perform the test on the biologic sample; and a printed circuit board (PCB) on a microfluidic reader, the PCB including a controller programmed to execute instructions, in response to a command received from the API, to instruct the microfluidic pumping and sensing region to perform the test based on a command received from the microfluidics application.

2. The microfluidics sensing system of claim 1, further comprising the API.

3. The microfluidics sensing system of claim 1, further comprising the microfluidics application to provide instructions to hardware with instructions on the microfluidic reader to perform the test.

4. The microfluidics sensing system of claim 1, wherein the portable computing device is coupled to the microfluidic chip by the microfluidic reader.

5. The microfluidics sensing system of claim 1, wherein the microfluidic chip is powered by the portable computing device.

6. The microfluidics sensing system of claim 1, wherein the test is performed at a voltage less than 15V.

7. The microfluidics sensing system of claim 1, wherein the command specifies the test to be performed by the microfluidic pumping and sensing region.

\* \* \* \* \*